(12) United States Patent
Wei et al.

(10) Patent No.: US 6,674,883 B1
(45) Date of Patent: Jan. 6, 2004

(54) SYSTEM AND METHOD FOR THE DETECTION OF ANATOMIC LANDMARKS FOR TOTAL HIP REPLACEMENT

(75) Inventors: Guo-Qing Wei, Plainsboro, NJ (US); Jianzhong Qian, Princeton, NJ (US); Helmuth Schramm, Neunkirchen (DE)

(73) Assignee: Siemens Corporate Research, Inc., Princeton, NJ (US)

( * ) Notice: Subject to any disclaimer, the term of this patent is extended or adjusted under 35 U.S.C. 154(b) by 472 days.

(21) Appl. No.: 09/638,122

(22) Filed: Aug. 14, 2000

(51) Int. Cl.[7] .................................................. G06K 9/00

(52) U.S. Cl. ........................................ 382/132; 382/195

(58) Field of Search ................................. 382/132, 128, 382/190, 195, 202, 203; 128/922

(56) References Cited

U.S. PATENT DOCUMENTS 5,610,966 A * 3/1997 Martell et al. ................ 378/58
5,824,085 A * 10/1998 Sahay et al. ................ 128/898

* cited by examiner

*Primary Examiner*—Leo Boudreau
*Assistant Examiner*—Ryan J. Miller
(74) *Attorney, Agent, or Firm*—Donald B. Paschburg; F. Chau & Associates, LLP

(57) ABSTRACT

A system and method for automatically detecting anatomical landmarks in a radiographic image, preferably for total hip replacement applications, in accordance with the present invention, provides a region of interest of the image, and determines a first landmark in the region of interest by computing an intensity ridge map. A second landmark is determined in the region of interest based on a position and orientation of the first landmark, and measurements are performed on the image based on positions of the first and second landmarks.

7 Claims, 5 Drawing Sheets

SYSTEM AND METHOD FOR THE DETECTION OF ANATOMIC LANDMARKS FOR TOTAL HIP REPLACEMENT

BACKGROUND

1. Technical Field

This disclosure relates to radiographic imaging, and more particularly, to a method for detecting anatomic landmarks in radiographic images, preferably for Total Hip Replacement (THR) applications.

2. Description of the Related Art

In Total Hip Replacement surgery, a prosthesis to be implanted in a patient should be chosen based on the size of the patient's anatomy. Typically, an X-ray image is first taken of the patient. Then, some specific landmarks on the radiograph are manually selected and measurements are made to find the most appropriate prosthesis from a database. This is referred to presently as pre-surgery planning. To determine whether a THR has been successful, regular follow-ups extending as long as 12 years need to be made. During these follow up visits, a set of landmarks need to selected from the radiographs, and measurements are made to determine the relative position changes of prosthetic components with respect to other bones over time.

The most common long-term problem following a THR is loosening. Wearing may also occur. Due to the large number of radiographs that need to be reviewed, the work overload for physicians is enormous. The most time-consuming part is the manual landmark selection. Depending on physician's experience and expert knowledge, this is also subject to inter-person and intra-person errors.

Therefore, a need exists for a fully automatic computer method for landmark detection and measurement for total hip replacement.

SUMMARY OF THE INVENTION

A method for automatically detecting anatomical landmarks in a radiographic image, in accordance with the present invention, provides a region of interest of the image, and determines a first landmark in the region of interest by computing an intensity ridge map. A second landmark is determined in the region of interest based on a position and orientation of the first landmark, and measurements are performed on the image based on positions of the first and second landmarks.

In other methods, the first landmark may include a femur, and the second landmark may include an outer boundary of the femur. The second landmark may alternately include a femoral head. The method may include the step of determining a next landmark in the region of interest based on a position and orientation of a previously determined landmark. The step of performing measurements may include the step of selecting a prosthesis based on a plurality of determined landmarks. The step of performing measurements may include the step of determining movement and wear of a prosthesis based on a plurality of determined landmarks. The first landmark may include a feature of a prosthetic femur, and the second landmark may include a portion of a pelvis.

A method for automatically detecting anatomical landmarks in a radiographic image of a hip, includes the steps of providing a radiographic image of a pelvis region, generating an intensity ridge map to highlight ridges in one direction, determining a position of a leg in the image by employing a strongest ridge in the ridge map to approximate the leg orientation and position, determining inner contour lines of a femur of the leg in the image based on a position and orientation of the strongest vertical ridge, determining outer surface lines of the femur based on a position and orientation of the inner contour lines and the ridge map, determining points of maximum curvature on a femoral head of the femur and tracing the femoral head by employing the ridge map, determining a center of the femoral head and selecting a prosthesis based on the inner contour lines, the points of maximum curvature and the center of the femoral head.

In other methods, the step of performing measurements on the image based on positions of determined landmarks may be included.

A method for automatically detecting anatomical landmarks in a radiographic image of a hip having a prosthesis, includes the steps of providing a radiographic image of a pelvis region, generating an intensity ridge map to highlight ridges in one direction, determining a position of a leg in the image by employing a strongest ridge in the ridge map to approximate the leg orientation and position, determining a boundary of the prosthesis in a femur of the leg in the image based on a position and orientation of the strongest ridge, determining a position of a femoral component head of the prosthesis by testing the boundary of the prosthesis in accordance with an expected shape, tracing an arcuate line of ilium by employing the position of the femoral component head and performing measurements to determine a degree of wear and loosening of the prosthesis.

In other methods, the step of tracing a boundary of an obturator foramen to find centers of the obturator foramen may be included. The method may include the step of determining a public symphsis based on the centers of the obturator foramen and the arcuate line of ilium.

The above methods may be implemented in a program storage device readable by machine, tangibly embodying a program of instructions executable by the machine to perform these method steps.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

The present invention provides a fully automatic method for the detection of anatomic landmarks for pre-surgery planning, post-operative check-ups in the total hip replacement and other anatomic feature detection and measurements. The present invention searches for most easily recognizable landmarks and then extends the search to other landmarks by using general knowledge about their relative positions. Hypothesis-and-test methods are proposed to detect some more complex landmarks of prosthesis. With the present invention, a computer or program storage device can automatically find the most appropriate prosthesis for a patient and assess the performance of a prosthesis and provide quantitative diagnostic measurements for physicians' surgery planning.

The present invention may also be employed in key landmark detection for imaging positioning checking, key landmark detection for leg-length and balance checking, and may include a method for drawing and performing quantitative analysis based upon the detected landmarks for digital radiography (DR) systems, especially for clinical orthopedic applications.

Although the present invention is illustratively described in terms of hips and hip replacement procedures, the present invention is much broader and should not be construed as limited to the illustrative example. Other applications for the present invention may be useful for other anatomical features, structures or procedures may be employed in accordance with the present invention. For example, the present invention may be employed for sizing prosthetic limbs, etc.

The present invention uses general knowledge about the relative positions between anatomies to guide the computer or program store device to search for the necessary landmarks. Starting from the most easily recognizable ones, the search will, step-by-step, extend to other landmarks. Evidence of different kinds is combined to drive the search. It should be understood that the elements shown in FIGS. 1, 4, and 5 may be implemented in various forms of hardware, software or combinations thereof. Preferably, these elements are implemented on one or more appropriately programmed general purpose digital computers having a processor and memory and input/output interfaces.

The computer system or program storage device automatically marks the important anatomies needed for both pre-surgery planning and post-operative checkup in the illustrative example, which follows. The computer system gives quantitative measurements as needed for pre-operative surgical planning and post-operative follow-ups, such as loosening checks. The present invention can be also used in landmark detection for imaging positioning checking, landmark detection for leg-length and balance checking, drawing on the image and quantitative analysis based upon the detected landmarks, for clinical orthopedic applications.

Figure 1:
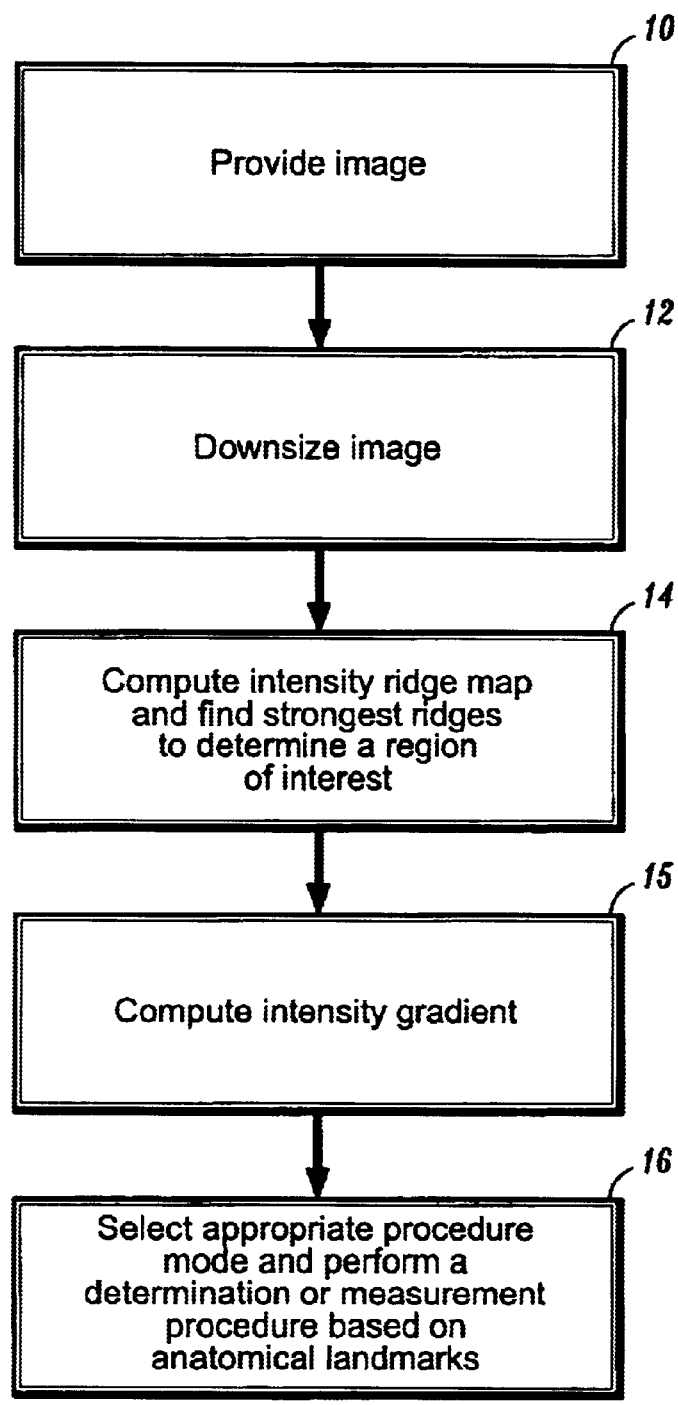
FIG. 1 is a block/flow diagram showing a system/method for detecting and processing a radiographic image in accordance with the present invention.
Figure 2:
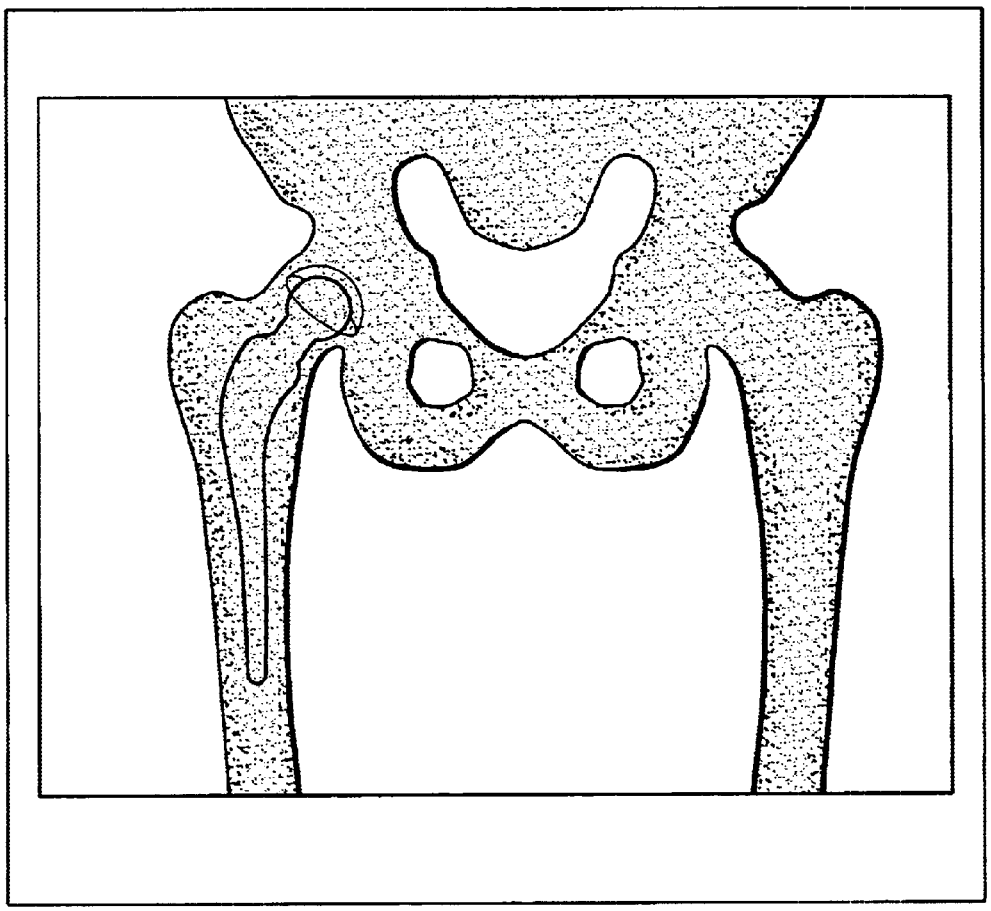
FIG. 2 depicts an image of a pelvis region for processing in accordance with the present invention.
Figure 3:
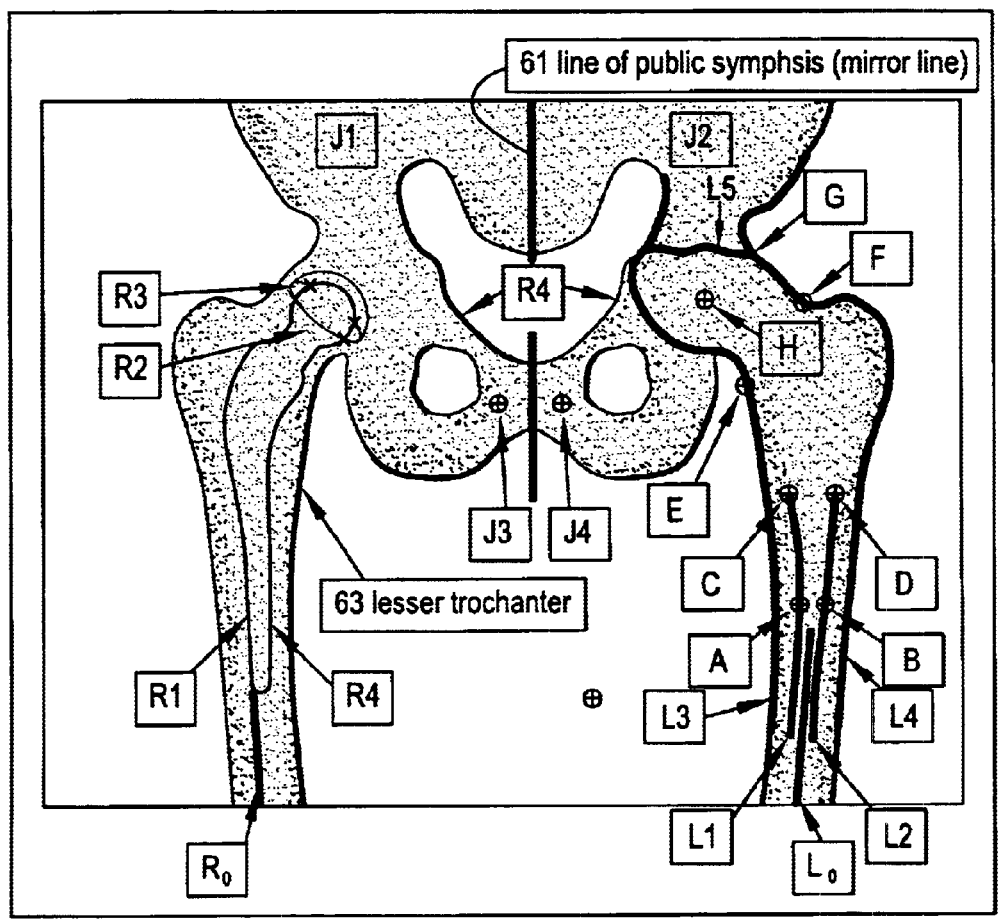
FIG. 3 depicts the image of the pelvis region of FIG. 2 having landmarks annotated in accordance with the present invention.

Referring now in specific detail to the drawings in which like reference numerals identify similar or identical elements throughout the several views, and initially to FIG. 1, a block/flow diagram is shown for a system/method of the present invention. The blocks of FIG. 1 will be described in detail with reference to FIGS. 2 and 3. FIG. 2 shows a hip image, while FIG. 3 is the same image overlaid with some detected landmarks.

An automatic search system/method includes the following components and/or steps. The method assumes that the image (FIG. 2) is oriented in the standing pose of humans. The detected landmarks are annotated on FIG. 3.

In block 10, an image (FIG. 2), preferably a digital image of a human being is provided. The image may include an X-ray, sonogram, or other radiographic image. In block 12, for an area of interest, such as the pelvic region, the image (FIG. 2) is downsized to a certain size (reduced, e.g., by compressing the pixels) followed by smoothing.

In block 14, an intensity ridge/valley map is then computed based on the intensity of pixels in the image. The ridge map computation is based on the second order derivatives of the intensity image in the horizontal, vertical and diagonal directions. A region of interest, for example, may be an upper leg region of the image. The system then finds the ridges of nearly vertical orientations, and locates strongest ridges $L_0$ and $R_0$ (e.g., highest or strongest intensity ridge), at a lower left and a lower right quarter of the image. This gives approximate locations of left and right legs ($L_0$ and $R_0$ in FIG. 3).

In block 15, a gradient intensity is computed for pixels in the image. A gradient map is computed based on the intensity differences in the horizontal and vertical directions, and the gradient map measures the rate of intensity change around each pixel. The gradient map highlights intensity edges in the input image. The gradient map will be employed as described below.

In block 16, the system performs a determination procedure. The system may include a plurality of different operational modes. Procedures performed by the system may be adjusted accordingly. For example, the system may use information about whether the procedure to be performed includes pre-surgery planning or an implant follow-up to switch to the correct detection mode. Measurements and determinations are made based on a landmark to landmark approach. In other words, a first found landmark is employed to determine a second landmark and so on.

Figure 4:
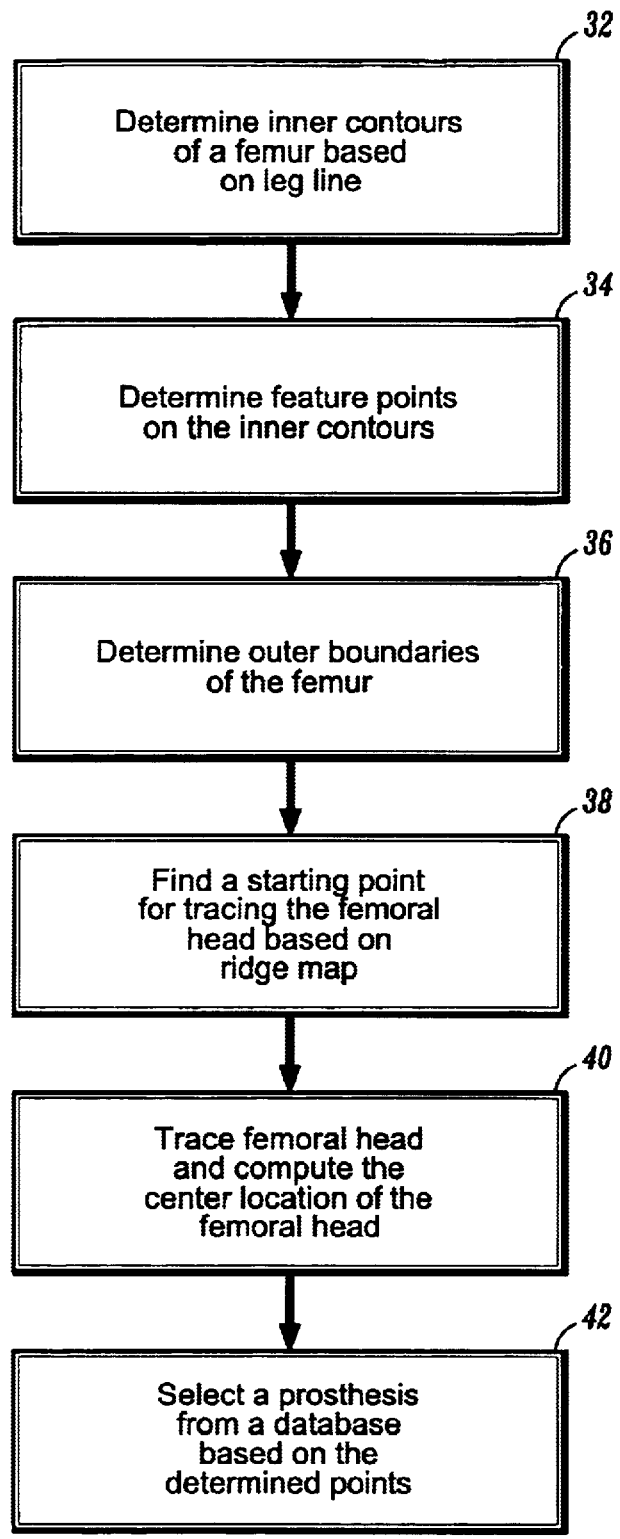
FIG. 4 is a block/flow diagram showing a system/method for determining a prosthesis size in accordance with the present invention.

Referring to FIG. 4, in the pre-surgery mode in block 16, the left leg is focused on for this example, which appears in the right half of the image (see FIG. 3).

In block 32, use the leg line $L_0$ detected in block 14 to define a search range. Trace two most interior contours of opposite contrast in parallel, with constraints on the distance between them being monotonic non-decreasing. This gives lines L1 and L2 in FIG. 3.

In block 34, feature points are found on the contours L1 and L2, in this example, two on each of the contours L1 and L2, with pre-specified distances in horizontal and vertical directions (points A, B, C, and D).

In block 36, two strongest contours L3 and L4 are traced, outside from the interior contours L1 and L2, with opposite gradient orientations at the starting points. The gradient orientation information is employed to ensure the correct starting points are chosen. Here, the gradient orientation of L3 is pointing toward the right, whereas that of L4 is toward the left. This gives the outer boundaries of the leg, L3 and L4. Points of the largest curvature are determined on each boundary (E and F).

In block 38, starting from the curvature maximum point F on the outer boundary L4, a starting point G is found for another part of the femoral head, using intensity ridge information obtained in block 12.

In block 40, beginning from point G, trace the boundary of the femoral head (curve L5), and then compute the center of the femoral head (point H) based on the physical characteristics denoted by L5 and the line between points E and F.

In block 42, the six points, A, B, C, D, E, F, and H, are used to give the measurements used to find a set of most suitable prosthesis from a prosthesis database. The physician may then decide which type of prosthesis to use.

Figure 5:
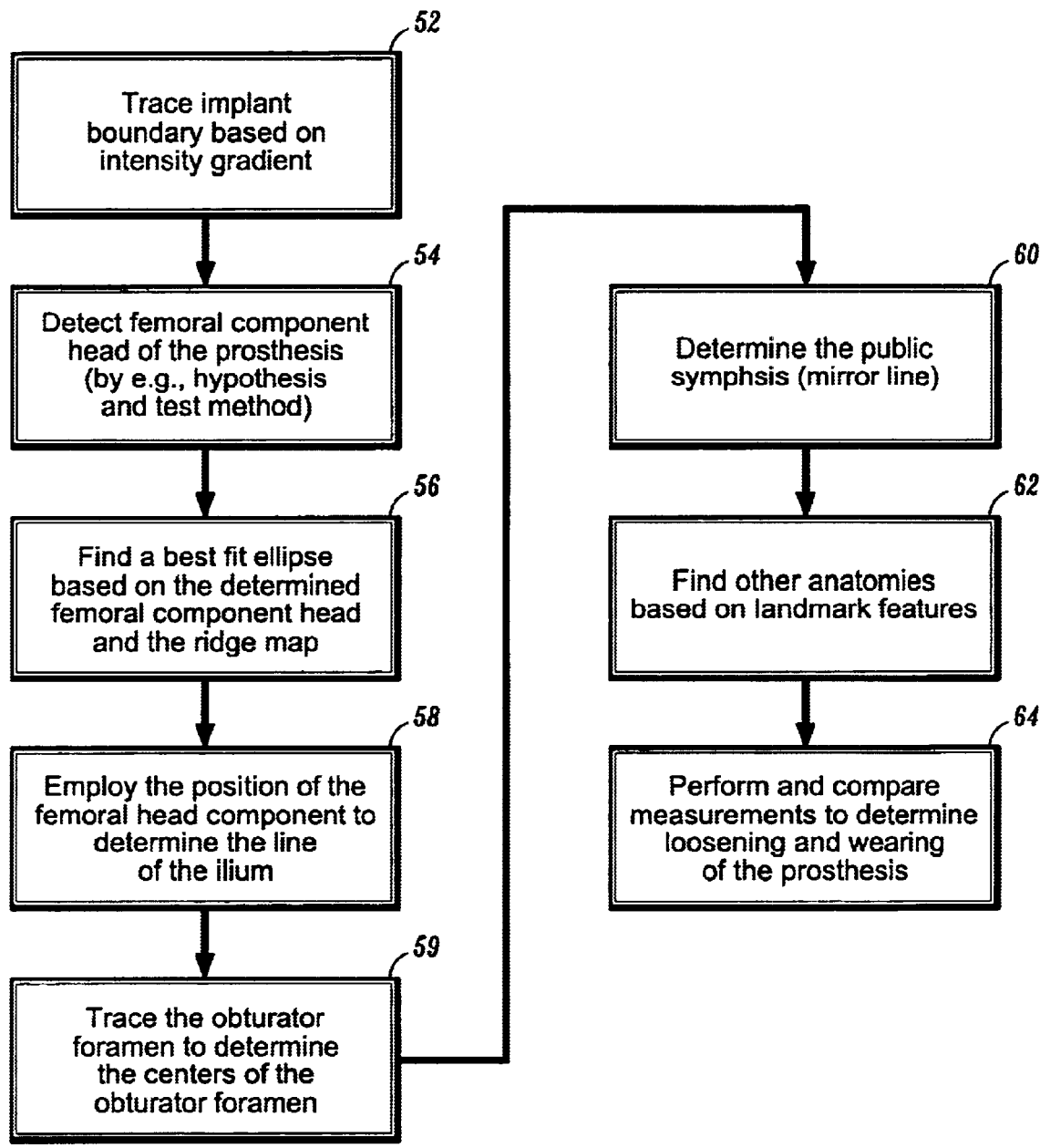
FIG. 5 is a block/flow diagram showing a system/method for measuring loosening or wear in a prosthesis in accordance with the present invention.

Referring to FIG. 5, in the follow-up mode in block 16, the right leg is focused on, for this example, which appears in the left half of the image (see FIG. 3).

In block 52, the position constraint exerted by the leg position line $R_0$ to trace the implant boundary (R1), based on the intensity gradient information of block 15. In block 54, a head of the prosthesis is detected by using a hypothesis-and-test method. This method includes, for example, for each point, say P1, on the implant boundary R1, choose two extra points, say P2 and P3, of specified distances from P1 on the implant boundary R1. A circle is fit to P1, P2 and P3 and points on the boundary R1 are found of a specified distance from the circle. This point set is denoted by S. The total angles spanned by all the points on S are computed with respect to the center of the circle, o. Suppose S={$S_1$, $S_2$, . . . $S_N$}, where $S_i$'S are the individual points on S, and the ordering of the individual points in S is that they trace the boundary R1 in a single direction (either clockwise or counter clockwise). Then, the angle spanned by S for the current point P1 is:

$$angle_{P1}=angle\ S_1OS_2+angle\ S_2OS_3+\ldots+angle\ S_{N-1}OS_N.$$

This computation is made for each point on the boundary R1. Then, the point set with a maximum angle spanning from all points on the boundary is found. The associated circle with the found set is chosen as the best fitting of the femoral component head, as indicated by R2 in FIG. 3. Other methods for locating the femoral component head may also be employed. The center and radius are measurements, which are to be used for diagnosis.

In block 56, for a WELLER implant type, from the points of the boundary R1 on the circle R2, find points of intersection (e.g., four points) of a contrast ring (R3) based on the intensity ridge map determined in block 14. Four crosses are indicated at the intersection of ring R3 and circle R2. These four points (crosses) are employed as constraints to find a best elliptical fitting to the ridge map (R3). The center, size, and orientation information are recorded for the ellipse.

In block 58, use the position constraint defined by the center of the femoral head to trace the arcuate line of ilium (R4), based on the intensity gradient on the arcuate line of ilium. Find the outermost points (J1 and J2) on the arcuate line of ilium. In block 59, the boundary of the obturator foramen is traced to find the centers of the obturator foramen (J3 and J4). In block 60, the outmost points on the arcuate line ilium (J1 and J2) and the centers of the obturator foramen (J3 and J4) are employed as references to find, for example, the line of public symphsis 61 (also called the mirror line). In block 62, positional relationships to the already found landmarks are employed to find other anatomies, such as for example, the lesser trochanter 63 (FIG. 3).

In block 64, the detected landmarks are also employed to perform automatic measurement and compare the measurements with those made in previous follow-ups to determine the degree of loosening or wearing.

The present invention advantageously employs spatial reasoning together with image evidence of different kinds to localize landmarks. The landmarks are not restricted to those listed above. Additional landmarks may be found, or different processing sequences may be employed to find the illustratively described landmarks or other landmarks. The present invention is also applicable to other regions of interest, for example, a skull, hands, feet, rib cage, etc. Advantageously, the present invention is trainable. A user, such as a physician can, for example, teach the computer what to detect by performing an example analysis. Then, the computer can automatically follow suit on new radiographs.

The decision as to what to compute, e.g., point-to-point or point-to-line distances, from the detected landmarks is up to a physician's or user's choice. Once it is specified, the computer automatically computes the specified measurements. Based on these measurements, the physician then makes his or her decisions concerning pre-surgery planning, degree of loosening and wearing of the prosthesis, or takes other diagnostic actions.

The decisions as to how to do surgery planning, how to use the quantitative measurements for different applications, as well as any diagnostic decisions according to the detected landmarks are made by physicians. The present invention avoids the tedious task of manually selecting regions by, for example, mouse clicking, and also offers a more objective and accurate way for performing the detection and measurement. Physicians can then focus more on the diagnostic part of the work rather than spending most of their time on collecting measurement data.

Having described preferred embodiments for system and method for the detection of anatomic landmarks (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for automatically detecting anatomical landmarks in a radiographic image of a hip, comprising the steps of:

providing a radiographic image of a pelvis region;

generating an intensity ridge map to highlight ridges in one direction;

determining a position of a leg in the image by employing a strongest ridge in the ridge map to approximate the leg orientation and position;

determining inner contour lines of a femur of the leg in the image based on a position and orientation of the strongest vertical ridge;

determining outer surface lines of the femur based on a position and orientation of the inner contour lines and the ridge map;

determining points of maximum curvature on a femoral head of the femur and tracing the femoral head by employing the ridge map;

determining a center of the femoral head; and selecting a prosthesis based on the inner contour lines, the points of maximum curvature and the center of the femoral head.

2. A program storage device readable by machine, tangibly embodying a program of instructions executable by the machine to perform method steps, as recited in claim 1.

3. The method as recited in claim 1, further comprising the step of performing measurements on the image based on positions of determined landmarks.

4. A method for automatically detecting anatomical landmarks in a radiographic image of a hip having a prosthesis, comprising the steps of:

provinding a radiographic image of a pelvis region;

generating an intensity ridge map to highlight ridges in one direction;

determining a position of a leg in the image by employing a strongest ridge in the ridge map to approximate the leg orientation and position;

determining a boundary of the prosthesis in a femur of the leg in the image based on a position and orientation of the strongest ridge;

determining a position of a femoral component head of the prosthesis by testing the boundary of the prosthesis in accordance with an expected shape;

tracing an arcuate line of ilium by employing the position of the femoral component head; and performing measurements to determine a degree of wear and loosening of the prosthesis.

5. A program storage device readable by machine, tangibly embodying a program of instructions executable by, the machine to perform method steps, as recited in claim 4.

6. The method as recited in claim 4, further comprising the step of tracing a boundary of an obturator foramen to find centers of the obturator foramen.

7. The method as recited in claim 4, further comprising the step of determining a public symphsis based on the centers of the obturator foramen and the arcuate line of ilium.

* * * * *